United States Patent
Choo et al.

(10) Patent No.: US 7,160,884 B2
(45) Date of Patent: Jan. 9, 2007

(54) 1-/2-SUBSTITUTED-1H/-2H-[1,2,3]TRIAZOLO[4,5-G]PHTHALAZINE-4,9-DIONE COMPOUND, PROCESS FOR THE PREPARATION THEREOF AND PHARMACEUTICAL COMPOSITION COMPRISING THE SAME

(75) Inventors: Hea Young Park Choo, Seoul (KR); Jin Sung Kim, Seoul (KR); Hee Kyung Rhee, Seoul (KR); Hyun Joo Park, Seoul (KR); Sang Kook Lee, Seoul (KR); Chong Ock Lee, Daejeon (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 11/330,073

(22) Filed: Jan. 12, 2006

(65) Prior Publication Data

US 2006/0217383 A1    Sep. 28, 2006

(30) Foreign Application Priority Data

Mar. 23, 2005   (KR) .................... 10-2005-0024154

(51) Int. Cl.
 *C07D 487/04* (2006.01)
 *A61K 31/5025* (2006.01)
(52) U.S. Cl. ..................... 514/248; 544/234
(58) Field of Classification Search ............. 544/234; 514/248
 See application file for complete search history.

*Primary Examiner*—Kahsay Habte
(74) *Attorney, Agent, or Firm*—Rothwell, Figg, Ernst & Manbeck, P.C.

(57) ABSTRACT

The present invention relates to 1-/2-substituted-1H/-2H-[1,2,3]triazolo[4,5-g]phthalazine-4,9-dione compounds and their pharmaceutically acceptable salts, a process for preparing the compounds and a pharmaceutical composition comprising the compounds. The compounds are shown to effectively inhibit cell proliferation and are thus expected to be used for treatment or prevention or treatment of various cancers or as an ancillary(auxiliary) means of the same.

11 Claims, No Drawings

1-/2-SUBSTITUTED-1H/-2H-[1,2,3]TRIAZOLO[4,5-G]PHTHALAZINE-4,9-DIONE COMPOUND, PROCESS FOR THE PREPARATION THEREOF AND PHARMACEUTICAL COMPOSITION COMPRISING THE SAME

TECHNICAL FIELD

The present invention relates to 1-/2-substituted-1H/-2H-[1,2,3]triazolo[4,5-g]phthalazine-4,9-dione compounds, a process for preparing the compounds and a pharmaceutical composition comprising the compounds.

RELATED PRIOR ART

Quinone compounds have been widely known to have various physiological activities [R. A. Morton, Ed. Biochemistry of Quinones(1965)]. Especially, heterocyclic quinone compounds are known to have an anticancer activity [G. A. Efimove, L. S. Efres, Zh. Org. Khim.(1967) 3, 162]. Examples of the heterocyclic quinone compounds are naphto-imidazoledione derivatives, imidazoquinolinedione derivatives, imidazo quinoxalinedione derivatives and imidazophthalazinedion derivatives.

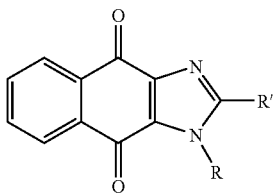

J. Med.Chem. 1996, 39.

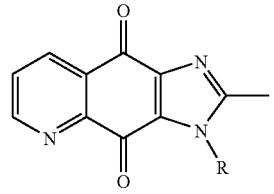

Bioorg. Med. Chem. 2000, 2079.

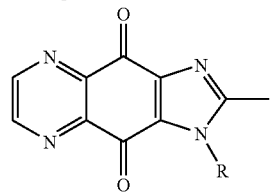

J. Med.Chem. 1998, 41.

However, 2-methyl-1-substituted-naphto[2,3-d]imidazole-4,9-dione and 2-methyl-1-substituted-imidazo[4,5-g]quinolinedione in the naphtoquinone derivatives have been reported to have a relatively low cytotoxicity [J. Med. Chem.(1996) 39, 1447; Bioorg. Med. Chem.(2000), 8, 2079]. Further, 2-methyl-4,9-dehydro-1-(4-bromophenyl)-1H-imidazo[4,5-g]-quinoxaline-4,9-dione also showed cytotoxicity against only human gastric cancer adenocarcinoma cell line although its cytotoxicity was reported to be higher than that of cisplatin or doxorubicin, which are currently used as an anticancer drug for the treatment of human gastric adenocarcinoma cell line [H. W. Yoo, et al., J. Med. Chem.(1998), 41, 4716]. Meanwhile, Korean patent publication No. 10-2005-17050 discloses 1-substituted-2-methyl-1H-imidazo[4,5-g]phthalazin-4,9-dione as the imidazophthalazine dione derivatives.

Shaikh et al. discovered that the number or position of nitrogen atoms in the heterocycle of heterocyclic quinone compounds plays an important role in an anticancer activity and that DNA intercalation activity increases in the order of naphthalene, quinoline and diazanaphthalene [I. A. Shaikh, et. al., J. Med. Chem.(1986), 29(8), 1335].

Therefore, the present inventors have performed extensive researches and found that triazolophthalazinedione derivatives with more nitrogen atoms in its cyclic phthalazine structure have a significantly enhanced anticancer activity, thereby completing the present invention.

SUMMARY OF INVENTION

In one aspect, the present invention is related to 1-/2-substituted-1H/-2H-[1,2,3]triazolo[4,5-g]phthalazine-4,9-dione.

In another aspect, the present invention is related to a process for preparing a mixture of the compounds of the 1-/2-substituted-1H/-2H-[1,2,3]triazolo[4,5-g]phthalazine-4,9-dione or a pharmaceutically acceptable salt thereof, the process comprising:

(a) preparing phthalazin-5,8-dione from phthalazine, (b) preparing 1-(4-methoxybenzyl)-1H-[1,2,3]triazolo[4,5-g]phthalazin-4,9-dione by reacting the phthalazine with 4-methoxybenzyl azide in a molar ratio of about 3 to about 1 in the presence of ethyl acetate, (c) preparing 1H-[1,2,3]triazolo[4,5-g]phthalazin-4,9-dione by dissolving the 1-(4-methoxybenzyl)-1H-[1,2,3]triazolo[4,5-g]phthalazin-4,9-dione in trifluoroacefic acid and subsequently performing reflux, and (d) alkylating the 1H-[1,2,3]triazolo[4,5-g]phthalazin-4,9-dione by using about 2–3 moles of potassium carbonate and about 2–3 moles of a halogenated alkylating agent with reference to one mole of the 1H-[1,2,3]triazolo[4,5-g]phthalazin-4,9-dione.

In still another aspect, the present invention is related to a pharmaceutical composition, comprising at least one compound of the 1-/2-substituted-1H/-2H-[1,2,3]triazolo[4,5-g]phthalazine-4,9-dione or a pharmaceutically acceptable salt thereof as an active ingredient.

In a still further aspect, the present invention is related to a method for treatment or prevention or adjuvant treatment of at least one disorder selected from the group consisting of gastric cancer, colon cancer, fibrosarcoma, myelogenous leukemia, lung cancer, ovarian cancer, melanoma and central nervous system tumor in a mammal which comprises administering to the mammal a therapeutically effective amount of the compound of the 1-/2-substituted-1H/-2H-[1,2,3]triazolo[4,5-g]phthalazine-4,9-dione or a pharmaceutically acceptable salt thereof.

DETAILED DESCRIPTION

In one aspect, the present invention is related to compounds of Formula I and II or a pharmaceutically acceptable salt thereof:

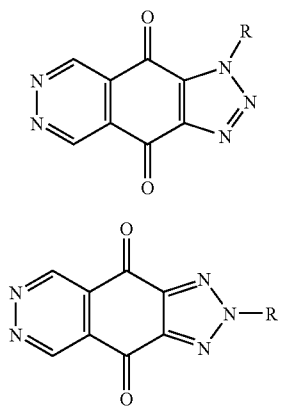

wherein R is selected from the group consisting of methyl, ethyl, n-propyl, isopropyl, n-butyl, isobutyl, sec-butyl, tert-butyl, n-pentyl, isopentyl, neopentyl, tert-pentyl, 1-metyl-butyl, 2-methylbutyl, 1,2-dimethylpropyl, n-hexyl, isohexyl, 1-methylpentyl, 2-methylpeptyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylbutyl, 1-ethyl-1-methylpropyl, 1-ethyl-2-methylpropyl, benzyl, 4-methoxybenzyl, phenyl, toluenyl, xylyl and cumenyl. Preferably, R is methyl, ethyl, n-propyl, n-butyl, or 4-methoxybenzyl.

Representative examples of the compound according to the present invention include, but are not limited to, 1-(4-methoxybenzyl)-1H-[1,2,3]triazolo[4,5-g]phthalazin-4,9-dione, 1H-[1,2,3]triazolo[4,5-g]phthalazin-4,9-dione, 1-methyl-1H-[1,2,3]triazolo[4,5-g]phthalazin-4,9-dione, 2-methyl-2H-[1,2,3]triazolo[4,5-g]phthalazin-4,9-dione, 1-ethyl-1H-[1,2,3]triazolo[4,5-g]phthalazin-4,9-dione, 2-ethyl-2H-[1,2,3]triazolo[4,5-g]phthalazin-4,9-dione, 1-n-propyl-1H-[1,2,3]triazolo[4,5-g]phthalazin-4,9-dione, 2-n-propyl-2H-[1,2,3]triazolo[4,5-g]phthalazin-4,9-dione, 1-n-butyl-1H-[1,2,3]triazolo[4,5-g]phthalazin-4,9-dione and 2-n-butyl-2H-[1,2,3]triazolo[4,5-g]phthalazin-4,9-dione.

As used herein, 'a heterocyclic quinone compound' refers to a compound having a structure wherein at least one heterocycle is fused with quinone cycle. As used herein, 'to be fused' is intended to mean to share one side of each cycle.

Compounds of the present invention have phthalazine as a main structure and also meet the following conditions required as DNA intercalater: (i) 3 or 4 planar fused cycles, (ii) heterocycle including two or more nitrogen atoms in a single cycle as a component forming the cycle, and (iii) conjugated carbonyl groups in para position relative to each other in the quinone structure.

B-DNA intercalation happens as the chromophore of intercalater, i.e. planar heterocyclic structure intercalates between the base pairs. While primary or secondary structure of DNA is not affected by the intercalation, tertiary structure changes to accept the planar intercalater. Particularly, tertiary structure becomes longer and looser as the distance between adjacent base pairs in a double helix increases due to the formation of an intercalater-DNA complex. This phenomenon appears to cause the compounds to inhibit the function of RNA polymerase, gyrase and topoisomerase and cell growth in S period, thereby rendering them with anticancer activities [Moore, M. H., Kennard, O. J. Mol. Biol. 206, 693, 1987; Pindur, U., Haber, M., Sattler, K. J. Chem. Educa. 70(4), 263, 1993; H. W. Yoo, et al., Bull. Korean Chem. Soc.(1997), 18, 484].

It has been known that hydrogen bond energy or van der Waals energy plays an important role in formation of stable intercalater-DNA complex [Kennard, O., Hunter, W. N. Angew. Chem. Int. Ed. Engl. 30, 1245, 1991]. The compounds of the present invention appear to contribute to the stability of the complex due to the presence of nitrogen atoms and carbonyl groups in the heterocyclic structure that can form a hydrogen bond with DNA.

Accordingly, the number or position of nitrogen atoms in the heterocylic structure plays an important role in exhibiting an anticancer activity. The compounds herein based on a phthalazine structure are more effective in the intercalation activity as compared with those with a quinoline or quinoxaline based structure. Further, para-positioned conjugated carbonyl groups are more preferable than ortho-positioned groups in formation of a stable complex.

Especially, the planar structure of plurality of heterocyles causes comparatively higher van der Waals energy due to the π electrons, which is advantageous in orientation and stacking with DNA and in formation of a more stable intercalation complex. However, DNA affinity for an intercalater decreases with the increase in the number of heterocyles and size of intercalater due to higher tendency of self-stacking. Therefore, 3 or 4 heterocyles (about 3–4 Å of height and about 6–8 Å of width), as claimed in the present invention, are preferred for achieving a more effective DNA intercalation.

In another aspect, the present invention is related to a process for preparing the compounds of Formulas I and II, as schematically shown in the Scheme 1, wherein R is as defined above.

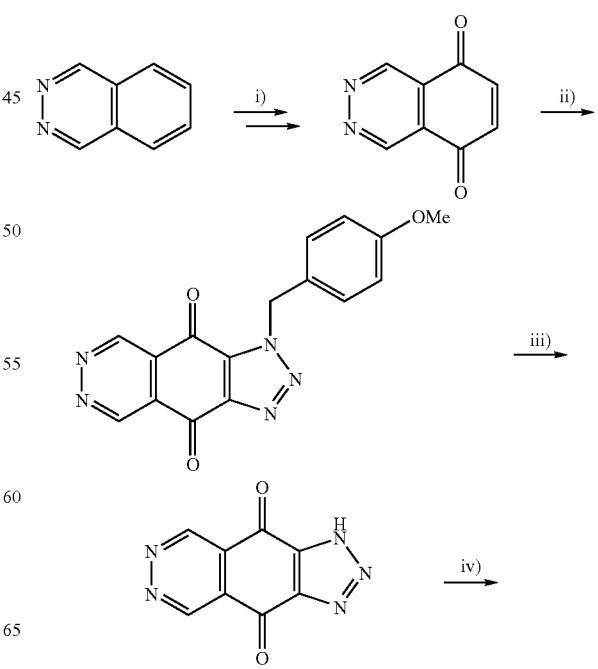

-continued

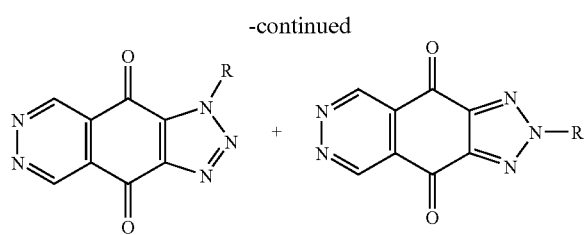

According to Scheme 1, (i) phthalazin-5,8-dione is prepared from the starting material, phthalzine, (ii) the phthalazin-5,8-dione is reacted with 4-methoxybenzyl azide in a molar ratio of about 3:1 in ethyl acetate, thereby providing 1-(4-methoxybenzyl)-1H-[1,2,3]triazolo[4,5-g] phthalazin-4,9-dione, (iii) the obtained compound is dissolved in TFA (trifluoroacetic acid) and the solution is refluxed, thus providing 1H-[1,2,3]triazolo[4,5-g]phthalazin-4,9-dione, (iv) the prepared compound is dissolved in DMF (dimethyl formamide) and is reacted with about 2–3 moles of potassium carbonate and about 2–3 moles of halogenated alkylating agent relative to one mole of the 1H-[1,2,3]triazolo[4,5-g]phthalazin-4,9-dione, thereby providing the desired compounds, 1-/2-substituted-1H/-2H-[1,2,3]triazolo[4,5-g]phthalazin-4,9-dione.

Thus, in an embodiment of the present invention, there is provided a process comprising the steps of (a) preparing phthalazin-5,8-dione from phthalazine, (b) preparing 1-(4-methoxybenzyl)-1H-[1,2,3]triazolo[4,5-g]phthalazin-4,9-dione by reacting the phthalazine with 4-methoxybenzyl azide in a molar ratio of about 3 to about 1 in the presence of ethyl acetate, (c) preparing 1H-[1,2,3]triazolo[4,5-g]phthalazin-4,9-dione by dissolving the 1-(4-methoxybenzyl)-1H-[1,2,3]triazolo[4,5-g]phthalazin-4,9-dione in trifluoroacetic acid and subsequently performing reflux, and (d) alkylating the 1H-[1,2,3]triazolo[4,5-g]phthalazin-4,9-dione by using potassium carbonate and halogenated alkylating agent in about 3 times molar equivalence, respectively, relative to 1H-[1,2,3]triazolo[4,5-g]phthalazin-4,9-dione.

Hereunder is provided a detailed explanation of the preparation process according to a 1,3-dipolar addition.

Methods disclosed in "John, P., Ramanaranjinie, R. J. Chem. Soc. Perkin Trans 1, 211, 1993., Derek, R. B., Caroline, J. M. R. J. Chem. Soc. Perkin Trans 1, 627, 1982." may be used as the above step (a).

The step (b) is refluxing phthalazin-5,8-dione and 4-methoxybenzyl azide in a molar ratio of 3:1 in ethyl acetate for 6–12 hours, thereby providing 1-(4-methoxybenzyl)-1H-[1,2,3]triazolo[4,5-g]phthalazin-4,9-dione. The reason for using three-fold molar equivalent phthalazin-5,8-dione with reference to one mole of 4-methoxybenzyl is because two molar equivalent phthalazin-5,8-dione is needed to oxidize hydroquinone into quinone. Accordingly, the yield is calculated based on the amount of 4-methoxybenzyl azide.

In the step (c), 1-(4-methoxybenzyl)-1H-[1,2,3]triazolo[4,5-g]phthalazin-4,9-dione prepared in the step (b) is dissolved in TFA and then refluxed for 40–50 hours. NaOH is added in remnants and washed with ethyl acetate, and then 1H-[1,2,3]triazolo[4,5-g]phthalazin-4,9-dione is obtained by acidifying the resulting aqueous layer to pH 1. Examples of halogenated alkylating agents include, but are not limited to, methyl iodide, ethyl iodide, propyl iodide and butyl iodide.

Thus obtained 1-/2-substituted-1H/-2H-[1,2,3]triazolo[4,5-g]phthalazin-4,9-dione compounds are racemic mixtures and may be separated from each other by using chromatography.

The 1H-[1,2,3]triazolo[4,5-g]phthalazin-4,9-dione derivatives were also produced according to the following Scheme 2.

Scheme 2

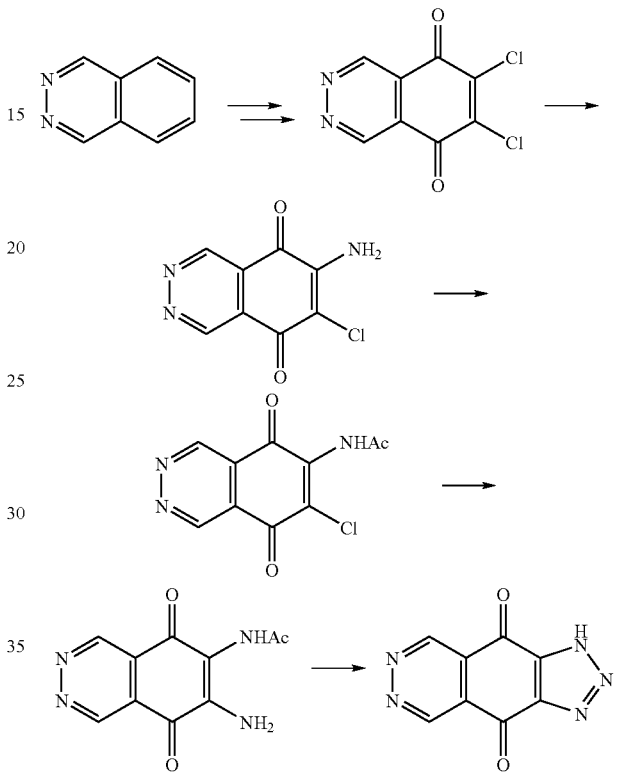

That is, 6,7-dichlorophthalazin-5,8-dione was prepared from phthalazine, and aminoacetamide derivatives are prepared by sequentially performing amination, acylation and reamination of the 6,7-dichlorophthalazin-5,8-dione. Finally, 1H-[1,2,3]triazolo[4,5-g]phthalazin-4,9-dione is obtained by diazotization of the aminoacetamide. However, this scheme comprises too many complicated steps and inevitably utilizes ammonia gas for direct amination of halide.

Therefore, the present invention provides an novel process for preparing 1H-[1,2,3]triazolo[4,5-g]phthalazin-4,9-dione through 1,3-dipolar addition.

Pharmaceutically acceptable salts of sufficiently basic compounds according to the present invention are, for example, acid additive salts. Representative examples of the acid additive salts include, but are not limited to, acid additive salts of inorganic or organic (such as chloric acid, hydrobromic acid, sulfuric acid, phosphoric acid, methanesulfonic acid, benzenesulfonic acid, trifluoroacetic acid, citric acid, lactic acid and maleic acid). Pharmaceutically acceptable salts of sufficiently acidic compounds according to the present invention are, for example, base additive salts. Examples of the base additive salts include, but are not limited to, alkali metal salts such as lithium, sodium or potassium salt; alkaline earth metal salts such as calcium or magnesium salts; ammonium salt or additive salts with base that gives physiologically acceptable cations such as methyl amine, dimethyl amine, trimethyl amine, piperidine, morpholine or tris-(2-hydroxyethyl)amine salts.

These salts are within the scope of the present invention and may be also prepared according to any known method. For example, these salts may be prepared by contacting the acidic or basic compounds in a stoichiometric ratio in an aqueous, non-aquous or partially aqueous solvent, and obtained by appropriate filtration, preferably after precipitation with a non-solvent such as ether or a hydrocarbon solvent, evaporation of the solvent or cold drying of the aqueous solvent.

In still another aspect, the present invention is related to a pharmaceutical composition, comprising at least one compound of the 1-/2-substituted-1H/-2H-[1,2,3]triazolo[4,5-g] phthalazine-4,9-dione or a pharmaceutically acceptable salt thereof as an active ingredient.

A pharmaceutical composition of the present invention has DNA intercalation activity and may be used for treatment or prevention or adjuvant treatment of abnormal proliferation (e.g. cancer) in human. Examples of the abnormal proliferation include, but are not limited to, various benign or malignant human tumors such as gastric cancer, colon cancer, sarcoma, leukemia, lung cancer, ovarian cancer, skin cancer, melanoma, central nervous system cancer, kidney cancer, liver cancer, bladder cancer, breast cancer, uterine carcinoma, prostate cancer, pancreatic cancer, vulvar cancer, thyroid cancer, gliomas and various head or neck tumors, and preferably gastric cancer, colon cancer, fibrosarcoma, myelogenous leukemia, lung cancer, ovarian cancer, melanoma and central nervous system tumor.

A pharmaceutical composition of the present invention may be formulated into a single unit or a multi dosage form by using a pharmaceutically acceptable carrier or an excipient, and may be administered once or several times via oral, parenteral or topical routes. As used herein, 'parenteral' includes without limitation subcutaneous, intravenous, intramuscular, or intrasternal injections or infusion techniques. As used herein, 'topical' includes without limitation delivery of the composition to mucosal tissue or skin of mouth or nose, and also includes spray inhalation and rectum administration Examples of formulation type a pharmaceutical composition herein include without limitation solid, semisolid or liquid forms (e.g. tablet, capsule, pill, powder, suppository, solution, Elixir, syrup, suspension, cream, sugar coated tablet, paste and spray). The administration route of the phthalazine derivatives herein may be selected depending on the formulation type as known in the art. A unit dosage form is preferred because it enables to easily handle and administer exact amount of an active compound. An active compound of the present invention may be comprised of a sufficient amount for providing a desired unit dosage, specifically in the amount of 0.1–95 wt % relative to that of the total composition.

A pharmaceutical composition is administered at a dose of 0.01–100 mg/kg per day based on an active ingredient in a unit or multiple dosage form, wherein the dosage may vary depending on an individual's physical conditions or pathological views.

For oral administration, a tablet containing various excipients such as sodium citrate, calcium carbonate and potassium phosphatedibasic may further comprise potato or tapioca starch, alginic aicd, disintegrants such as a silicate complex and binders such as poly(vinyl pyrrolidone), sucrose, gelatin and Arabian gum. Further, lubricants such as magnesium stearate, sodium laurylsulfate and talc are very useful for tablet formulation. A similar form of a solid composition may be used as a filler in a soft or hard gelatin capsule. Examples of preferred material include lactose or poly(ethylene glycol). When an aqueous suspending agent or Elixir is preferred to orally administered, necessary active ingredient may be admixed with various sweetening agent or flavors; coloring agent or pigment; if necessary emulsion agent and/or suspending agents; and water, ethanol, propylene glycol, glycerin and similar various diluents.

For parenteral administration, conventional materials may be also used in the present invention as carrier, adjuvant and vehicle. Injection solution such as oily solution, suspension or emulsion may be formulated according to the conventional method by using appropriate disintegrant, wetting agent or suspending agents. A parenterally acceptable non-toxic diluent or a solvent such as a sterilized non-exothermic material or 1,3-butandiol may be used to prepare a sterilized injection. Examples of other acceptable vehicle or solvent include 5% dextrose injection, linger injection and NaCl isotonic injection. Further, a sterilized nonvolatile oil is conventionally used as a solvent or a suspending medium. A mixture including synthetic mono-, di-triglyceride or other kinds of nonvolatile oils may also be used for this purpose. Fatty acids such as oleic acid may be used for preparing an injection solution.

Suppositories for rectum administration may be formulated by admixing active compounds herein with an appropriate non-irritating excipient such as cocoa butter or poly (ethylene glycol), which is solid at room temperature but melts in rectum, thus providing drugs.

Further, a pharmaceutical composition of the present invention may also be administered via topical route, preferably in a form of cream, salves, jelly, paste or ophthalmic ointment according to standard pharmaceutical formulation.

In a further aspect, the present invention is related to a method for treatment or prevention or adjuvant treatment of at least one disorder selected from the group consisting of gastric cancer, colon cancer, fibrosarcoma, myelogenous leukemia, lung cancer, ovarian cancer, melanoma and central nervous system tumor in a mammal which comprises administering to the mammal a therapeutically effective amount of the compound of the 1-/2-substituted-1H/-2H-[1, 2,3]triazolo[4,5-g]phthalazine-4,9-dione or a pharmaceutically acceptable salt thereof.

EXAMPLES

The present invention is described more specifically by the following Examples. Examples herein are meant only to illustrate the present invention, but in no way to limit the claimed invention.

Example 1

Preparation of
1H-[1,2,3]triazolo[4,5-g]phthalazin-4,9-dione (a) Preparation of 1-(4-methoxybenzyl)-1H-[1,2,3] triazolo[4,5-g]phthalazin-4,9-dione 333 mg (2.07 mmol) of phthalazin-5,8-dione (1.00 g, 6.20 mmol) and 4-methoxybenzyl azide were dissolved in 60 ml of ethyl acetate, and then refluxed overnight. The solvent was removed under reduced pressure and residue was separated and purified by using column chromatography (ethyl acetate). 415 mg of brown powder was obtained and the yield was 62%.

Boiling point: >270° C.
$^1$H-NMR(CDCl$_3$): δ 10.04(d, J=1.2, 1H), 9.94(d, J=1.2, 1H), 7.47(d, J=8.8, 2H), 6.87(d, J=8.8, 2H), 5.96(s, 2H), 3.78(s, 3H)
IR(CH$_2$Cl$_2$): 1697, 1515 cm$^{-1}$
HR-FABMS (for C$_{16}$H$_{12}$O$_3$N$_5$ (M$^+$+1)):
Calculated value: 322.0940;
Measured value: 322.0943

(b) Preparation of 1H-[1,2,3]triazolo[4,5-g]phthalazin-4,9-dione 415 mg (1.29 mmol) of 1-(4-methoxybenzyl)-1H-[1,2,3]triazolo[4,5-g]phthalazin-4,9-dione was dissolved in 30 ml of TFA and refluxed for 2 days. TFA was removed under reduced pressure and 100 ml of 1M NaOH was added to residue, followed by washing with ethyl acetate. The resulting aqueous layer was acidified to pH 1 with HCl, and extracted with ethyl acetate. 150 mg of light brown powder was obtained by drying and concentrating the organic layer (yield 58%).

Boiling point: >270° C.
$^1$H-NMR(CD$_3$OD): δ 9.74(s, 2H)
IR(KBr): 1712, 1492 cm$^{-1}$
HR-FABMS: C$_8$H$_4$O$_2$N$_5$ (M$^+$+1)
Calculated value: 202.0365
Measured value: 202.0362

Example 2

Preparation of 1-methyl/2-methyl-1H-/2H-[1,2,3]triazolo[4,5-g]phthalazin-4,9-dione 70.0 mg (0.35 mmol) of 1H-[1,2,3]triazolo[4,5-g]phthalazin-4,9-dione, prepared according to Example 1, was dissolved in DMF. After 144 mg (1.04 mmol) of potassium carbonate and 148 mg (1.04 mmol) of methyl iodide (MeI) were added, the mixture was stirred at room temperature for 5 hours, filtered over Celite™ and extracted with ethyl acetate, followed by separation and filtration by using column chromatography (hexane:ethyl acetate=1:2).

(a) 1-methyl-1H-[1,2,3]triazolo[4,5-g]phthalazin-4,9-dione

Yield: 36% (apricot solid, 27 mg)
Boiling point: >270° C.
$^1$H-NMR(CDCl$_3$): δ 10.07(d, J=1.2, 1H), 9.96(d, J=1.2, 1H), 4.55(s, 3H)
IR(CH$_2$Cl$_2$): 1693, 1498 cm$^{-1}$
HR-FABMS: C$_9$H$_6$O$_2$N$_5$ (M$^+$+1)
Calculated value: 216.0521
Measured value: 216.0522

(b) 2-methyl-2H-[1,2,3]triazolo[4,5-g]phthalazin-4,9-dione

Yield: 20% (light brown solid, 15 mg)
Boiling point: >270° C.
$^1$H-NMR(CDCl$_3$): δ 10.03(s, 2H), 4.54(s, 3H)
IR(CH$_2$Cl$_2$): 1705, 1500 cm$^{-1}$
HR-FABMS: C$_9$H$_6$O$_2$N$_5$ (M$^+$+1)
Calculated value: 216.0521
Measured value: 216.0517

Example 3

Preparation of 1-ethyl/2-ethyl-1H/-2H-[1,2,3]triazolo[4,5-g]phthalazin-4,9-dione 100.0 mg (0.5 mmol) of 1H-[1,2,3]triazolo[4,5-g]phthalazin-4,9-dione, prepared according to Example 1, was dissolved in DMF. After 207 mg (1.49 mmol) of potassium carbonate and 233 mg (1.49 mmol) of ethyl iodide (EtI) were added, the mixture was stirred at room temperature for 5 hours, filtered over Celite™ and extracted with ethyl acetate, followed by separation and filtration by using column chromatography (hexane:ethyl acetate=1:2).

(a) 1-ethyl-1H-[1,2,3]triazolo[4,5-g]phthalazin-4,9-dione

Yield: 21% (light brown solid, 24 mg)
Boiling point: >270° C.
$^1$H-NMR(CDCl$_3$): δ 9.98(d, J=1.2, 1H), 9.89(d, J=1.2, 1H), 4.87(q, J=7.2, 2H), 1.62(t, J=7.2, 3H)
IR(CH$_2$Cl$_2$): 1698, 1493 cm$^{-1}$
HR-FABMS: C$_{10}$H$_8$O$_2$N$_5$ (M$^+$+1)
Calculated value: 230.0678
Measured value: 230.0683

(b) 2-ethyl-2H-[1,2,3]triazolo[4,5-g]phthalazin-4,9-dione

Yield: 29% (yellow solid, 33 mg)
Boiling point: >270° C.
$^1$H-NMR(CDCl$_3$): δ 9.96(s, 2H), 4.73(q, J=7.2, 2H), 1.69(t, J=7.2, 3H)
IR(CH$_2$Cl$_2$): 1705, 1500 cm$^{-1}$
HR-FABMS: C$_{10}$H$_8$O$_2$N$_5$ (M$^+$+1)
Calculated value: 230.0678
Measured value: 230.0676

Example 4

Preparation of 1-n-propyl/2-n-propyl-1H/-2H-[1,2,3]triazolo[4,5-g]phthalazin-4,9-dione 70.0 mg (0.35 mmol) of 1H-[1,2,3]triazolo[4,5-g]phthalazin-4,9-dione, prepared according to Example 1, was dissolved in DMF. After 144 mg (1.04 mmol) of potassium carbonate and 177 mg (1.04 mmol) of propyl iodide ($^n$PrI) were added, the mixture was stirred at room temperature for 5 hours, filtered over Celite™ and extracted with ethyl acetate, followed by separation and filtration by using column chromatography (hexane:ethyl acetate=1:2).

(a) 1-n-propyl-1H-[1,2,3]triazolo[4,5-g]phthalazin-4,9-dione

Yield: 18% (brown solid, 15 mg)
Boiling point: >270° C.
*$^1$H-NMR(CDCl$_3$): δ 10.07(s, 1H), 9.96(s, 1H), 4.86(br s, 2H), 2.04–2.12(m, 2H), 1.03(t, J=7.6, 3H)
IR(CH$_2$Cl$_2$): 1698, 1538 cm$^{-1}$
HR-FABMS: C$_{11}$H$_{10}$O$_2$N$_5$ (M$^+$+1)
Calculated value: 244.0834
Measured value: 244.0831

(b) 2-n-propyl-2H-[1,2,3]triazolo[4,5-g]phthalazin-4,9-dione

Yield: 27% (brown solid, 23 mg)
Boiling point: >270° C.
$^1$H-NMR(CDCl$_3$): δ 10.02(s, 2H), 4.71(t, J=7.2, 2H), 2.14–2.21(m, 2H) 1.01(t, J=7.6, 3H)
*124IR(CH$_2$Cl$_2$): 1704, 1496 cm$^{-1}$
HR-FABMS: C$_{11}$H$_{10}$O$_2$N$_5$ (M$^+$+1)
Calculated value: 244.0834
Measured value: 244.0835

Example 5

Preparation of 1-n-butyl/2-n-butyl-1H-2-H-[1,2,3]triazolo[4,5-g]phthalazin-4,9-dione 57.0 mg (0.28 mmol) of 1H-[1,2,3]triazolo[4,5-g]phthalazin-4,9-dione, prepared according to Example 1, was dissolved in DMF. After 117 mg (0.85 mmol) of potassium carbonate and 156 mg (0.85 mmol) of butyl iodide (BuI) were added, the mixture was stirred at room temperature for 5 hours, filtered over Celite™ and extracted with ethyl acetate, followed by separation and filtration by using column chromatography (hexane:ethyl acetate=1:2).

(a) 1-n-butyl-1H-[1,2,3]triazolo[4,5-g]phthalazin-4,9-dione

Yield: 8% (orange solid 6 mg)
Boiling point: >270° C.
$^1$H-NMR(CDCl$_3$): δ 10.05(d, J=1.2, 1H), 9.95(d, J=1.2, 1H), 4.88(t, J=7.6, 2H), 1.97–2.06(m, 2H), 1.37–1.47(m, 2H), 1.00(t, J=7.2, 3H)
IR(CH$_2$Cl$_2$): 1697, 1492 cm$^{-1}$
HR-FABMS: C$_{12}$H$_{12}$O$_2$N$_5$ (M$^+$+1)
Calculated value: 258.0991
Measured value: 258.0989

(b) 2-n-butyl-2H-[1,2,3]triazolo[4,5-g]phthalazin-4,9-dione

Yield: 28% (yellow solid, 20 mg)
Boiling point: >270° C.
$^1$H-NMR(CDCl$_3$): δ 10.03(s, 2H), 4.75(t, J=7.2, 2H), 2.08–2.17(m, 2H), 1.37–1.44(m, 2H), 0.99(t, J=7.2, 3H)
IR(CH$_2$Cl$_2$): 1704, 1495 cm$^{-1}$
HR-FABMS: C$_{12}$H$_{12}$O$_2$N$_5$ (M$^+$+1)
Calculated value: 258.0991
Measured value: 258.0988

Example 6

Measurement of Cytotoxicity

To verify the cytotoxic effect of the compounds prepared in Examples above, cytotoxicity was induced in cancer cells and SRB (Sulforhodamin B dye-staining) evaluation was conducted.

Cancer cell lines used herein (NCI, US) was human gastric cancer cell line (SNU-638), human colon cancer cell line (Col2), human fibrosarcoma cell line (HT1080), and human myelogenous leukemia cell line (HL-60).

Each compound prepared in Examples was dissolved in 10% DMSO. 10 μL of the solution and 190 μL of cell suspension (5×10$^4$ cells/ml) were placed in standard 96-well plate and cultured in 5% CO$_2$ condition at 37° C. for 3 days. 190 μL of the same cell suspension was placed in at least 16 wells, followed by cultivation at 37° C. for 30 minutes, and used as zero-day control. After cultivation for a predetermined period of time, cells were fixed by adding 50 μL of 50% trichloroacetic acid in each well, followed by incubation at 4° C. for 30 minutes. Cells were washed with water 5 times, dried at room temperature, and stained by adding 100 μL of 1% acetic acid solution containing 4% SRB in each well, and then washed with 1% acetic acid after 1 hour and dried in air. 200 μL of 10 mM Tris-base was added in each well and stirred well, thereby dissolving the bound staining agent, followed by measurement of absorbance at 515 nm by using ELISA reader. Viability was determined based on the difference between the zero-day control group and 10% DMSO-treated control group. Viability about ellipticin and doxorubicin were also measured for comparison. IC$_{50}$ (μM) was determined from the viability values relative to control group, and is provided in the following TABLE 1.

TABLE 1

| Material | SNU-638 | Col2 | HT1080 | HL-60 |
| --- | --- | --- | --- | --- |
| Ellipticin | 2.99 | 2.619 | 1.929 | 3.366 |
| Doxorubicin | 0.052 | 0.098 | 0.022 | 0.044 |
| Example 1a | 0.257 | 2.383 | 0.330 | 0.130 |
| Example 1b | >5 | >5 | >5 | >5 |
| Example 2a | 0.241 | 0.311 | 0.073 | 0.082 |
| Example 2b | 0.054 | 0.132 | 0.0078 | 0.124 |
| Example 3a | 0.126 | 0.341 | 0.068 | 0.056 |
| Example 3b | 0.046 | 0.170 | 0.204 | 0.090 |
| Example 4a | 0.212 | 0.353 | 0.075 | 0.083 |
| Example 4b | 0.043 | 0.057 | 0.033 | 0.157 |
| Example 5a | 0.155 | 0.421 | 0.099 | 0.089 |
| Example 5b | 0.050 | 0.066 | 0.030 | 0.151 |

Meanwhile, SRB evaluation was also conducted for human lung cancer cell line (A549), human ovarian cancer cell line (SK-OV-3), human melanoma cell line (SK-MEL-2), human central nervous system tumor cell line (XF498), and human colon cancer cell line (HCT15), and the results are shown in TABLE 2.

TABLE 2

| Material | A549 | SK-OV-3 | SK-MEL-2 | XF498 | HCT15 |
| --- | --- | --- | --- | --- | --- |
| Ellipticin | 1.32 | 1.47 | 2.41 | 3.64 | 3.72 |
| Doxorubicin | 0.022 | 0.041 | 0.019 | 0.044 | 0.251 |
| Example 1a | 0.054 | 0.012 | 0.041 | 0.118 | 0.059 |
| Example 1b | 9.02 | 7.64 | >10.00 | >10.00 | >10.00 |
| Example 2a | 0.004 | 0.003 | 0.008 | 0.035 | 0.103 |
| Example 2b | 0.002 | 0.0004 | 0.002 | 0.004 | 0.020 |
| Example 3a | 0.006 | 0.003 | 0.008 | 0.034 | 0.039 |
| Example 3b | 0.018 | 0.003 | 0.004 | 0.017 | 0.018 |
| Example 4a | 0.026 | 0.014 | 0.020 | 0.085 | 0.176 |
| Example 4b | 0.019 | 0.009 | 0.009 | 0.018 | 0.018 |
| Example 5a | 0.081 | 0.021 | 0.023 | 0.181 | 0.177 |
| Example 5b | 0.018 | 0.017 | 0.015 | 0.019 | 0.018 |

As provided in TABLEs 1 & 2, all compounds in Examples 2–5 were much superior to ellipticin in cytotoxicity, and a few tens of times superior over doxorubicin.

It was also verified that 2-substituted compounds have a higher cytotoxic effect than 1-substituted compounds. Especially, 2-methyl-2H-[1,2,3]triazolo[4,5-g]phthalazin-4,9-dione prepared in Example 2b showed the highest cytotoxicity against human fibrosarcoma cell line (HT1080), human lung cancer cell line (A549), human ovarian cancer cell line (SK-OV-3), human melanoma cell line (SK-MEL-2) and human central nervous system cancer cell line (XF498).

Therefore, 1-/2-substituted-1H/-2H-[1,2,3]triazolo[4,5-g] phthalazin-4,9-dione compounds of the present invention may be used for treating or preventing various cancers, especially gastric cancer, colon cancer, fibrosarcoma, myelogenous leukemia, lung cancer, ovarian cancer, melanoma and central nervous system cancer.

What is claimed is:

1. A compound of Formula I or a pharmaceutically acceptable salt thereof:

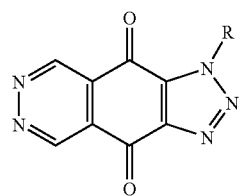

(I)

wherein R is selected from the group consisting of methyl, ethyl, n-propyl, isopropyl, n-butyl, isobutyl, sec-butyl, tert-butyl, n-pentyl, isopentyl, neopentyl, tert-pentyl, 1-metylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylbutyl, 1-ethyl-1-methylpropyl, 1-ethyl-2-methylpropyl, benzyl, 4-methoxybenzyl, phenyl, toluenyl, xylyl and cumenyl.

2. A compound of Formula II or a pharmaceutically acceptable salt thereof:

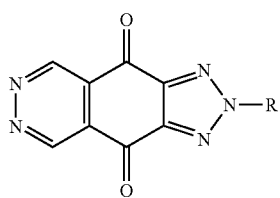

(II)

wherein R is selected from the group consisting of hydrogen, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, benzyl, 4-methoxybenzyl, phenyl, toluenyl, xylenyl and cumenyl.

3. A compound or a pharmaceutically acceptable salt thereof according to claim 1, wherein R is selected from hydrogen, methyl, ethyl, n-propyl and n-butyl.

4. A compound or a pharmaceutically acceptable salt thereof according to claim 2, wherein R is selected from hydrogen, methyl, ethyl, n-propyl and n-butyl.

5. A compound selected from the group consisting of:
(i) 1-(4-methoxybenzyl)-1H-[1,2,3]triazolo[4,5-g]phthalazin-4,9-dione,
(ii) 1H-[1,2,3]triazolo[4,5-g]phthalazin-4,9-dione,
(iii) 1-methyl-1H-[1,2,3]triazolo[4,5-g]phthalazin-4,9-dione,
(iv) 2-methyl-2H-[1,2,3]triazolo[4,5-g]phthalazin-4,9-dione,
(v) 1-ethyl-1H-[1,2,3]triazolo[4,5-g]phthalazin-4,9-dione,
(vi) 2-ethyl-2H-[1,2,3]triazolo[4,5-g]phthalazin-4,9-dione,
(vii) 1-n-propyl-1H-[1,2,3]triazolo[4,5-g]phthalazin-4,9-dione,
(viii) 2-n-propyl-2H-[1,2,3]triazolo[4,5-g]phthalazin-4,9-dione,
(ix) 1-n-butyl-1H-[1,2,3]triazolo[4,5-g]phthalazin-4,9-dione, and
(x) 2-n-butyl-2H-[1,2,3]triazolo[4,5-g]phthalazin-4,9-dione.

6. A process for preparing a mixture of compounds of Formulas I and II or a pharmaceutically acceptable salt thereof, the process comprising:
(a) preparing phthalazin-5,8-dione from phthalazine,
(b) preparing 1-(4-methoxybenzyl)-1H-[1,2,3]triazolo[4,5-g]phthalazin-4,9-dione by reacting the phthalazine with 4-methoxybenzyl azide in a molar ratio of about 3 to about 1 in the presence of ethyl acetate,
(c) preparing 1H-[1,2,3]triazolo[4,5-g]phthalazin-4,9-dione by dissolving the 1-(4-methoxybenzyl)-1H-[1,2,3]triazolo[4,5-g]phthalazin-4,9-dione in trifluoroacetic acid and subsequently performing reflux, and
(d) alkylating the 1H-[1,2,3]triazolo[4,5-g]phthalazin-4,9-dione by using about 2–3 times molar equivalent of potassium carbonate and about 2–3 times molar equivalent of halogenated alkylating agent;

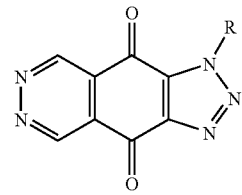

(I)

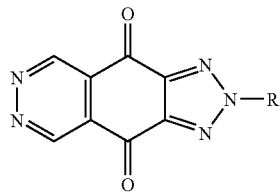

(II)

wherein R is selected from the group consisting of hydrogen, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, phenyl, toluenyl, xylenyl and cumenyl.

7. A pharmaceutical composition, comprising at least one compound of the Formula I according to claim 1 or a pharmaceutically acceptable salt thereof as an active ingredient and a pharmaceutically acceptable carrier.

8. A pharmaceutical composition, comprising at least one compound of the Formula II according to claim 2 or a pharmaceutically acceptable salt thereof as an active ingredient and a pharmaceutically acceptable carrier.

9. A pharmaceutical composition, comprising at least one compound of the Formula I according to claim 3 or a pharmaceutically acceptable salt thereof as an active ingredient and a pharmaceutically acceptable carrier.

10. A pharmaceutical composition, comprising at least one compound of the Formula II according to claim 4 or a pharmaceutically acceptable salt thereof as an active ingredient and a pharmaceutically acceptable carrier.

11. A pharmaceutical composition, comprising at least one compound according claim 5 or a pharmaceutically acceptable salt thereof as an active ingredient and a pharmaceutically acceptable carrier.

\* \* \* \* \*